(12) United States Patent
Kimmich et al.

(10) Patent No.: US 7,518,014 B2
(45) Date of Patent: Apr. 14, 2009

(54) MODIFIED SUPPORT MATERIALS FOR CATALYSTS

(75) Inventors: Barbara Kimmich, League City, TX (US); Leslie E. Wade, Pearland, TX (US); Tao Wang, Houston, TX (US); André Harmen Sijpkes, Almere (NL); Roelandus Hendrikus Wilhelmus Moonen, Alkmaar (NL)

(73) Assignee: Celanese International Corp., Dallas, TX (US)

( * ) Notice: Subject to any disclaimer, the term of this patent is extended or adjusted under 35 U.S.C. 154(b) by 332 days.

(21) Appl. No.: 11/285,436

(22) Filed: Nov. 21, 2005

(65) Prior Publication Data

US 2006/0135809 A1    Jun. 22, 2006

Related U.S. Application Data

(60) Provisional application No. 60/637,529, filed on Dec. 20, 2004.

(51) Int. Cl.
C07C 67/00 (2006.01)
(52) U.S. Cl. .................................................... 560/241
(58) Field of Classification Search ................. 560/241
See application file for complete search history.

(56) References Cited

U.S. PATENT DOCUMENTS

| | | | |
|---|---|---|---|
| 3,441,601 A | 4/1969 | Sennewald et al. | |
| 3,470,230 A | 9/1969 | Hirsch et al. | |
| 3,775,342 A | 11/1973 | Kronig et al. | |
| 3,822,308 A | 7/1974 | Kronig et al. | |
| 4,087,622 A | 5/1978 | Nakamura et al. | |
| 4,340,504 A | 7/1982 | Courty et al. | |
| 4,420,420 A | 12/1983 | Mita et al. | |
| 4,764,498 A | 8/1988 | Wissner et al. | |
| 4,902,823 A | 2/1990 | Wunder et al. | |
| 4,977,126 A | 12/1990 | Mauldin et al. | |
| 5,185,308 A | 2/1993 | Bartley et al. | |
| 5,194,417 A | 3/1993 | Smith et al. | |
| 5,200,382 A | 4/1993 | Cody et al. | |
| 5,274,181 A | 12/1993 | Bartley et al. | |
| 5,314,858 A | 5/1994 | Colling | |
| 5,332,710 A | 7/1994 | Nicolau et al. | |
| 5,336,802 A | 8/1994 | Smith et al. | |
| 5,342,987 A | 8/1994 | Bartley | |
| 5,466,652 A | 11/1995 | Paparizos et al. | |
| 5,559,071 A | 9/1996 | Abel et al. | |
| 5,567,839 A | 10/1996 | Gulliver et al. | |
| 5,576,457 A | 11/1996 | Abel | |
| 5,688,993 A * | 11/1997 | Provine ....................... 560/245 |
| 5,691,267 A | 11/1997 | Nicolau et al. | |
| 5,700,753 A | 12/1997 | Wang et al. | |
| 5,808,136 A | 9/1998 | Tacke et al. | |
| 5,859,287 A | 1/1999 | Nicolau et al. | |
| 5,935,889 A | 8/1999 | Murrell et al. | |
| 5,990,344 A | 11/1999 | Couves et al. | |
| 6,015,769 A | 1/2000 | Wang | |
| 6,017,847 A | 1/2000 | Wang | |
| 6,022,823 A | 2/2000 | Augustine et al. | |
| 6,034,030 A | 3/2000 | Nicolau et al. | |
| 6,057,260 A | 5/2000 | Nicolau et al. | |
| 6,107,513 A | 8/2000 | Herzog et al. | |
| 6,107,514 A | 8/2000 | Nicolau et al. | |
| 6,114,571 A | 9/2000 | Abel et al. | |
| 6,114,573 A | 9/2000 | Herzog | |
| 6,143,921 A | 11/2000 | Karim et al. | |
| 6,156,927 A | 12/2000 | Halcom et al. | |
| 6,225,496 B1 | 5/2001 | Baker et al. | |
| 6,258,978 B1 | 7/2001 | Kitchen et al. | |
| 6,268,522 B1 | 7/2001 | Hagemeyer et al. | |
| 6,303,537 B1 | 10/2001 | Wang et al. | |
| 6,342,628 B1 | 1/2002 | Williams et al. | |
| 6,346,501 B1 | 2/2002 | Herzog et al. | |
| 6,350,900 B1 | 2/2002 | Wang et al. | |
| 6,350,901 B1 | 2/2002 | Kitchen et al. | |
| 6,358,882 B1 | 3/2002 | Salem et al. | |
| 6,376,706 B2 | 4/2002 | Kitchen et al. | |
| 6,399,813 B1 | 6/2002 | Blum et al. | |
| 6,407,283 B2 | 6/2002 | Couves et al. | |
| 6,420,308 B1 | 7/2002 | Khanmamedova | |
| 6,448,432 B2 | 9/2002 | Williams | |

(Continued)

FOREIGN PATENT DOCUMENTS

CA    820352    8/1969

(Continued)

*Primary Examiner*—Rei-tsang Shiao
(74) *Attorney, Agent, or Firm*—Simmons Perrine PLC

(57) ABSTRACT

The present invention relates to a method of producing a catalyst or pre-catalyst suitable for assisting in the production of alkenyl alkanoates. The method includes contacting a modifier precursor to a support material to form a modified support material. One or more catalytic component precursors (palladium or gold) may be contacted to the modified support material. The atomic ratio of gold to palladium is preferably in the range of about 0.3 to about 0.90. The support materials with the catalytic component may then be reduced using a reducing environment. A composition for catalyzing the production of an alkenyl alkanoates including a modified support material with palladium and gold is also included within the invention. Catalysts of the present invention may be used to produce alkenyl alkanoates in general and vinyl acetate in particular and are useful to produce low EA/VA ratios while maintaining or improving $CO_2$ selectivity.

14 Claims, No Drawings

U.S. PATENT DOCUMENTS

| | | | |
|---|---|---|---|
| 6,472,556 | B2 | 10/2002 | Kitchen et al. |
| 6,486,093 | B2 | 11/2002 | Wang et al. |
| 6,486,370 | B1 | 11/2002 | Rende et al. |
| 6,492,299 | B1 | 12/2002 | Couves et al. |
| 6,603,038 | B1 | 8/2003 | Hagemeyer et al. |
| 2001/0048970 | A1 | 12/2001 | Hagemeyer et al. |
| 2002/0013220 | A1 | 1/2002 | Wang et al. |
| 2002/0016495 | A1 | 2/2002 | Williams |
| 2002/0058833 | A1 | 5/2002 | Cirjak et al. |
| 2002/0188152 | A1 | 12/2002 | Khanmamedova |
| 2002/0198404 | A1 | 12/2002 | Herzog et al. |
| 2003/0059356 | A1 | 3/2003 | Hoke et al. |
| 2003/0109746 | A1 | 6/2003 | Fiorentino et al. |
| 2003/0148883 | A1 | 8/2003 | Khanmamedova |
| 2003/0161775 | A1 | 8/2003 | Rodemerck et al. |
| 2003/0166466 | A1 | 9/2003 | Hoke et al. |

FOREIGN PATENT DOCUMENTS

| | | |
|---|---|---|
| DE | 19914066 A1 | 10/2000 |
| DE | 10030039 A1 | 1/2002 |
| EP | 0347830 A2 | 6/1989 |
| EP | 0569624 | 11/1993 |
| EP | 0634208 | 7/1994 |
| EP | 0634209 | 7/1994 |
| EP | 0654301 | 5/1995 |
| EP | 0672453 | 9/1995 |
| EP | 0685449 | 12/1995 |
| EP | 0685451 | 12/1995 |
| EP | 0871604 | 5/1996 |
| EP | 0891226 | 3/1997 |
| EP | 0847982 | 6/1998 |
| EP | 0997192 | 9/1998 |
| EP | 0891224 | 1/1999 |
| EP | 0898494 | 3/1999 |
| EP | 1015108 | 6/2001 |
| EP | 0723810 | 7/2001 |
| EP | 0906151 | 7/2001 |
| EP | 0874798 | 8/2001 |
| EP | 0986433 | 8/2001 |
| EP | 0877727 | 11/2001 |
| EP | 0909213 | 11/2001 |
| EP | 1164123 | 12/2001 |
| EP | 0827422 | 2/2002 |
| EP | 0839793 | 3/2002 |
| EP | 1230977 | 8/2002 |
| EP | 1102635 | 10/2002 |
| EP | 1106247 | 3/2003 |
| EP | 1323469 | 7/2003 |
| JP | 10081508 | 3/1998 |
| JP | 10139727 | 5/1998 |
| JP | 10195021 | 7/1998 |
| JP | 10328571 | 12/1998 |
| JP | 11009997 | 1/1999 |
| JP | 11244696 | 9/1999 |
| JP | 11244697 | 9/1999 |
| JP | 11268017 | 10/1999 |
| JP | 11349534 | 12/1999 |
| JP | 2000169430 | 12/1999 |
| JP | 2000000473 | 1/2000 |
| JP | 2000063324 | 2/2000 |
| JP | 2000063325 | 2/2000 |
| JP | 2000063326 | 2/2000 |
| JP | 2000086335 | 3/2000 |
| JP | 2000119219 | 4/2000 |
| JP | 2000176285 | 6/2000 |
| JP | 2000218152 | 8/2000 |
| JP | 2002030036 | 6/2001 |
| WO | WO 94/21374 | 9/1994 |
| WO | WO 97/33690 | 9/1997 |
| WO | WO 97/36678 | 10/1997 |
| WO | WO 97/36679 | 10/1997 |
| WO | WO 97/37759 | 10/1997 |
| WO | WO 97/38790 | 10/1997 |
| WO | WO 97/44130 | 11/1997 |
| WO | WO 98/00232 | 1/1998 |
| WO | WO 98/05620 | 2/1998 |
| WO | WO 98/52688 | 11/1998 |
| WO | WO 98/55225 | 12/1998 |
| WO | WO 98/55443 | 12/1998 |
| WO | WO 99/08790 | 2/1999 |
| WO | WO 99/21650 | 5/1999 |
| WO | WO 99/22863 | 5/1999 |
| WO | WO 99/29418 | 6/1999 |
| WO | WO 99/29419 | 6/1999 |
| WO | WO 99/30818 | 6/1999 |
| WO | WO 99/39824 | 8/1999 |
| WO | WO 99/42212 | 8/1999 |
| WO | WO 99/51339 | 10/1999 |
| WO | WO 99/62632 | 12/1999 |
| WO | WO 99/62633 | 12/1999 |
| WO | WO 99/62634 | 12/1999 |
| WO | WO 00/07727 | 2/2000 |
| WO | WO 00/44496 | 8/2000 |
| WO | WO 00/51962 | 9/2000 |
| WO | WO 00/58008 | 10/2000 |
| WO | WO 00/66261 | 11/2000 |
| WO | WO 00/69802 | 11/2000 |
| WO | WO 01/00559 | 1/2001 |
| WO | WO 01/07496 | 2/2001 |
| WO | WO 01/36091 | 5/2001 |
| WO | WO 01/36092 | 5/2001 |
| WO | WO 01/90042 | 11/2001 |
| WO | WO 01/90043 | 11/2001 |
| WO | WO 02/04392 | 1/2002 |

* cited by examiner

MODIFIED SUPPORT MATERIALS FOR CATALYSTS

CLAIM OF PRIORITY

The application claims the benefit of U.S. application 60/637,529, filed on Dec. 20, 2004, which is hereby incorporated by reference.

FIELD OF THE INVENTION

The present invention relates to catalysts, methods of making the catalysts, and methods of making alkenyl alkanoates. More particularly, the invention relates to catalysts, methods of making the catalysts, and methods of making vinyl acetate.

BACKGROUND OF THE INVENTION

Certain alkenyl alkanoates, such as vinyl acetate (VA), are commodity chemicals in high demand in their monomer form. For example, VA is used to make polyvinyl acetate (PVAc), which is used commonly for adhesives, and accounts for a large portion of VA use. Other uses for VA included polyvinyl alcohol (PVOH), ethylene vinyl acetate (EVA), vinyl acetate ethylene (VAE), polyvinyl butyral (PVB), ethylene vinyl alcohol (EVOH), polyvinyl formal (PVF), and vinyl chloride-vinyl acetate copolymer. PVOH is typically used for textiles, films, adhesives, and photosensitive coatings. Films and wire and cable insulation often employ EVA in some proportion. Major applications for vinyl chloride-vinyl acetate copolymer include coatings, paints, and adhesives often employ VAE having VA in some proportion. VAE, which contains more than 50 percent VA, is primarily used as cement additives, paints, and adhesives. PVB is mainly used for under layer in laminated screens, coatings, and inks. EVOH is used for barrier films and engineering polymers. PVF is used for wire enamel and magnetic tape.

Because VA is the basis for so many commercially significant materials and products, the demand for VA is large, and VA production is frequently done on a relatively large scale, e.g. 50,000 metric tons or more per year. This large scale production means that significant economies economies of scale are possible and relatively subtle changes in the process, process conditions or catalyst characteristics can have a significant economic impact on the cost of the production of VA.

Many techniques have been reported for the production of alkenyl alkanoates. For example, in making VA, a widely used technique includes a catalyzed gas phase reaction of ethylene with acetic acid and oxygen, as seen in the following reaction:

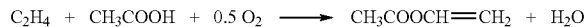

$$C_2H_4 + CH_3COOH + 0.5\,O_2 \longrightarrow CH_3COOCH=CH_2 + H_2O$$

Several side reactions may take place, including, such as, the formation of $CO_2$. The results of this reaction are discussed in terms of the space-time yield (STY) of the reaction system, where the STY is the grams of VA produced per liter of catalyst per hour of reaction time (g/l*h).

The composition of the starting material feed can be varied within wide limits. Typically, the starting material feed includes 30-70% ethylene, 10-30% acetic acid and 4-16% oxygen. The feed may also include inert materials such as $CO_2$, nitrogen, methane, ethane, propane, argon and/or helium. The primary restriction on feed composition is the oxygen level in the effluent stream exiting the reactor must be sufficiently low such that the stream is outside the flammability zone. The oxygen level in the effluent is affected by the oxygen level in the starting material stream, $O_2$ conversion rate of the reaction and the amount of any inert material in the effluent.

The gas phase reaction has been carried out where a feed of the starting materials is passed over or through fixed bed reactors. Successful results have been obtained through the use of reaction temperatures in the range of 125° C. to 200° C., while reaction pressures of 1-15 atmospheres are typical.

While these systems have provided adequate yields, there continues to be a need for reduced production of by-products, higher rates of VA output, and lower energy use during production. One approach is to improve catalyst characteristics, particularly as to $CO_2$ selectivity and/or activity of the catalyst. Another approach is to modify reaction conditions, such as the ratio of starting materials to each other, the $O_2$ conversion of the reaction, the space velocity (SV) of the of the starting material feed, and operating temperatures and pressures.

The formation of $CO_2$ is one aspect which may be reduced through the use of improved catalysts. The $CO_2$ selectivity is the percentage of the ethylene converted that goes to $CO_2$. Decreasing the $CO_2$ selectivity permits a larger amount of VA per unit volume and unit time in existing plants, even retaining all other reaction conditions.

The formation of ethyl acetate (EA) is another aspect which may be reduced through the use of improved catalysts. The EA selectivity is usually expressed in ppm as the ratio EA/VA wt/wt. Decreasing the EA selectivity permits reducing or eliminating post-production purification of VA. By reducing the EA selectivity of a catalyst, the processing steps associated with EA removal could be eliminated, thus providing cost savings. It would be desirable to achieve an EA/VA ratio less than the typical ratio of about 700 ppm, preferably less than about 200 ppm without sacrificing the catalysts' $CO_2$ selectivity or its activity.

Attempts to reduce EA output have included increasing the gold to palladium ratio on the catalyst, such as shown in U.S. Pat. No. 5,185,308. While this patent indicates that the EA/VA ratio eventually goes to zero with a high enough gold to palladium ratio, experimental testing has been unable to reproduce this result. Furthermore, $CO_2$ selectivity is sacrificed through the use of an increased gold to palladium ratio. Consequently, another approach is needed.

VA output of a particular reaction system is affected by several other factors including the activity of the catalyst, the ratio of starting materials to each other, the $O_2$ conversion of the reaction, the space velocity (SV) of the starting material feed, and operating temperatures and pressures. All these factors cooperate to determine the space-time yield (STY) of the reaction system, where the STY is discussed in terms of grams of VA produced per liter of catalyst per hour of reaction time or g/l*h.

Generally, activity is a significant factor in determining the STY, but other factors may still have a significant impact on the STY. Typically, the higher the activity of a catalyst, the higher the STY the catalyst is able to produce.

The $O_2$ conversion is a measure of how much oxygen reacts in the presence of the catalyst. The $O_2$ conversion rate is temperature dependent such that the conversion rate generally climbs with the reaction temperature. However, the $CO_2$ selectivity also increases along with the increase in temperature. Thus, the $O_2$ conversion rate is selected to give the desired VA output balanced against the amount of $CO_2$ produced. A catalyst with a higher activity means that the overall reaction temperature can be lowered while maintaining the same $O_2$ conversion. Alternatively, a catalyst with a higher activity will give a higher $O_2$ conversion rate at a given temperature and space velocity.

It is common that catalysts employ one or more catalytic components carried on a relatively inert support material. In the case of VA catalysts, the catalytic components are typically a mixture of metals that may be distributed uniformly throughout the support material ("all through-out catalysts"), just on the surface of the support material ("shell catalysts"), just below a shell of support material ("egg white catalysts") or in the core of the support material ("egg yolk catalysts"). Preferred type of metal distribution is dependent a number of factors including the reactor system and catalyst size/shape.

Numerous different types of support materials have been suggested for use in VA catalyst including silica, cerium doped silica, alumina, titania, zirconia and oxide mixtures. But very little investigation of the differences between the support materials has been done. For the most part, only silica and alumina have actually been commercialized as support materials.

One useful combination of metals for VA catalysis is palladium and gold. Pd/Au catalysts provide adequate $CO_2$ selectivity and activity, but there continues to be a need for improved catalysts given the economies of scale that are possible in the production of VA.

One process for making Pd/Au catalysts typically includes the steps of impregnating the support with aqueous solutions of water-soluble salts of palladium and gold; reacting the impregnated water-soluble salts with an appropriate alkaline compound e.g., sodium hydroxide, to precipitate (often called fixing) the metallic elements as water-insoluble compounds, e.g. the hydroxides; washing the fixed support material to remove un-fixed compounds and to otherwise cleanse the catalyst of any potential poisons, e.g. chloride; reducing the water insoluble compounds with a typical reductant such as hydrogen, ethylene or hydrazine, and adding an alkali metal compound such as potassium or sodium acetate.

Various modifications to this basic process have been suggested. For example, in U.S. Pat. No. 5,990,344, it is suggested that sintering of the palladium be undertaken after the reduction to its free metal form. In U.S. Pat. No. 6,022,823, it suggested that calcining the support in a non-reducing atmosphere after impregnation with both palladium and gold salts might be advantageous. In WO94/21374, it is suggested that after reduction and activation, but before its first use, the catalyst may be pretreated by successive heating in oxidizing, inert, and reducing atmospheres.

In U.S. Pat. No. 5,466,652, it is suggested that salts of palladium and gold that are hydroxyl-, halide- and barium-free and soluble in acetic acid may be useful to impregnate the support material. A similar suggestion is made in U.S. Pat. No. 4,902,823, i.e. use of halide- and sulfur-free salts and complexes of palladium soluble in unsubstituted carboxylic acids having two to ten carbons.

In U.S. Pat. No. 6,486,370, it suggested that a layered catalyst may be used in a dehydrogenation process where the inner layer support material differs from the outer layer support material. Similarly, U.S. Pat. No. 5,935,889 suggests that a layered catalyst may useful as acid catalysts. But neither suggests the use of layered catalysts in the production of alkenyl alkanoates. In U.S. Patent Publication 2005/0181940, layered catalysts for vinyl acetate are shown, but modified support materials are not.

In U.S. Pat. No. 5,808,136 it suggested that a titanium or zirconium may be used to pre-treat a silica or alumina support material to improved activity and/or $CO_2$ selectivity of the catalyst.

Taken together, the inventors have recognized and addressed the need for continued improvements in the field of VA catalysts to provide improved VA production at lower costs.

SUMMARY OF THE INVENTION

The present invention relates to a method of producing a catalyst or pre-catalyst suitable for assisting in the production of alkenyl alkanoates. The method includes contacting a modifier precursor to a support material to form a modified support material. One or more catalytic component precursors (palladium and/or gold) may be contacted to the modified support material. The atomic ratio of gold to palladium is preferably in the range of about 0.3 to about 0.90. The support materials with the catalytic component may then be reduced using a reducing environment and/or activated using with an activating agent such as KOAc. A composition for catalyzing the production of an alkenyl alkanoates including a modified support material with palladium and gold is also included within the invention. Catalysts of the present invention may be used to produce alkenyl alkanoates in general and vinyl acetate in particular.

DETAILED DESCRIPTION

Catalysts

For present purposes, a catalyst is any support material that contains at least one catalytic component and that is capable of catalyzing a reaction, whereas a pre-catalyst is any material that results from any of the catalyst preparation steps discussed herein.

Catalysts and pre-catalysts of the present invention may include those having a modified support material. Effective use of the catalyst accordingly should help improve EA selectivity while maintaining or improving $CO_2$ selectivity, activity or both, particularly as pertaining to VA production. Moreover, the combination of improving EA selectively while maintaining or improving $CO_2$ selectivity may be desirable even if activity is adversely affected.

It should be appreciated that the present invention is described in the context of certain illustrative embodiments, but may be varied in any of a number of aspects depending on the needs of a particular application. By way of example, without limitation, the catalysts may have the catalytic components uniformly distributed throughout the support material or they may be shell catalysts where the catalytic components are found in a relatively thin shell around a support material core. Egg white catalysts may also be suitable, where the catalytic components reside substantially away from the center of support material. Egg yolk catalysts may also be suitable. suitable. Preferred type of metal distribution is dependent on a number of factors including the reactor system and catalyst size/shape and include shell catalysts and layered catalysts.

Catalytic Components

In general, the catalysts and pre-catalysts of the present invention include metals and particularly include a combination of at least two metals. In particular, the combination of metals includes at least one from Group VIIIB and at least one from Group IB. It will be appreciated that "catalytic component" is used to signify the metal that ultimately provides catalytic functionally to the catalyst, but also includes the metal in a variety of states, such as salt, solution, sol-gel, suspensions, colloidal suspensions, free metal, alloy, or combinations thereof. Preferred catalysts include palladium and gold as the catalytic components.

Another preferred embodiment of the catalyst includes between about 1 to about 10 grams of palladium and preferably between about 1 and 10 grams of palladium per liter.

In one embodiment for catalysts, Au to Pd atomic ratios between about 0.1 and about 1.25 may be preferred for catalysts. Most preferred Au:Pd atomic ratios are from 0.3-0.9. The atomic ratio can be adjusted to balance the EA/VA selectivity and $CO_2$ selectivity. Employment of higher Au/Pd weight or atomic ratios tends to favor relatively lower EA/VA ratios but higher $CO_2$ selectivity.

One embodiment is the use of ground or powder catalysts for screening of catalyst compositions. A ground catalyst may be one where the catalytic components are contacted to the support material followed by a reduction in the particle size (e.g. by grinding or ball milling) or one where the catalytic components are contacted to the support material after the support material has been reduced in size. In one embodiment, a ground or powder catalyst is used to simulate a shell catalyst. In simulated shell catalyst, an aliquot of support material with a relatively high concentration of modifiers and/or catalytic components is diluted with a support material that is substantially free of modifiers and/or catalytic component, but has been activated with an activation agent (e.g. potassium acetate), as discussed below. The diluted support material then has the preferred amounts of modifiers and/or catalytic components in the catalyst.

For shell catalysts, the thickness of the shell of catalytic components on the support material ranges from about 5 μm to about 500 μm. More preferred ranges include from about 5 μm to about 300 μm.

Support Materials

In one aspect of the invention, the catalytic components of the present invention generally will be carried by a support material. Suitable support materials typically include materials that are substantially uniform in identity or a mixture of materials. Overall, the support materials are typically inert in the reaction being performed. Support materials may be composed of any suitable substance preferably selected so that the support materials have a relatively high surface area per unit mass or volume, such as a porous structure, a molecular sieve structure, a honeycomb structure, or other suitable structure. For example, the support material may contain silica, alumina, silica-alumina, titania, titano-silicate, zirconia, zircono-silicate, niobia, silicates, alumino-silicates, titanates, spinel, silicon carbide, silicon nitride, carbon, cordierite, steatite, bentonite, clays, metals, glasses, quartz, pumice, zeolites, non-zeolitic molecular sieves combinations thereof and the like. Any of the different crystalline form of the materials may also be suitable, e.g. alpha or gamma alumina. Zirconia, zircono-silicates and titano-silicates containing support materials are the most preferred. In addition, multilayer support materials are also suitable for use in the present invention.

The support material in the catalyst of this invention may be composed of particles having any of various regular or irregular shapes, such as spheres, tablets, cylinders, discs, rings, stars, or other shapes. The support material may have dimensions such as diameter, length or width of about 1 to about 10 mm, preferably about 3 to about 9 mm. In particular having a regular shape (e.g. spherical) will have as its preferred largest dimension of about 4 mm to about 8 mm. In addition, a ground or powder support material may be suitable such that the support material has a regular or irregular shape with a diameter of between about 10 microns and about 1000 micron, with preferred sizes being between about 10 and about 700 microns, with most preferred sizes being between about 180 microns and about 450 microns. Larger or smaller sizes may be employed, as well as polydisperse collections of particles sizes. For example, for a fluid bed bed catalyst a preferred size range would include 10 to 150 microns. For precursors used in layered catalysts, a size range of 10 to 250 microns is preferred.

Surface areas available for supporting catalytic components, as measured by the BET (Brunauer, Emmett, and Teller) method, may generally be between about 1 $m^2/g$ and about 500 $m^2/g$, preferably about 20 $m^2/g$ to about 200 $m^2/g$. For example, for a porous support, the pore volume of the support material may generally be about 0.1 to about 2 ml/g, and preferably about 0.4 to about 1.2 ml/g. An average pore size in the range, for example, of about 50 to about 2000 angstroms is desirable, but not required.

Examples of suitable silica containing support materials include KA160 from Sud Chemie, Aerolyst350 from Degussa and other pyrogenic or microporous-free silicas with a particle size of about 1 mm to about 10 mm.

Examples of suitable zirconia containing support materials include those from NorPro, Zirconia Sales (America), Inc., Daichi Kigenso Kagaku Kogyo, Engelhard and Magnesium Elektron Inc (MEI). Suitable zirconia support materials have a wide range of surface areas from less than about 5 $m^2/g$ to more than 300 $m^2/g$. Preferred zirconia support materials have surface areas from about 20 $m^2/g$ to about 150 $m^2/g$, with a range of between about 30 $m^2/g$ and about 100 $m^2/g$ more preferred. Support materials may have their surfaces treated through a calcining step in which the virgin support material is heated. The heating reduces the surface area of the support material (e.g. calcining). This provides a method of creating support materials with specific surface areas that may not otherwise be readily available from suppliers.

Examples of other suitable support materials include titano-silicates from Grace such as SP18-9534 (silica with 0.61% $TiO_2$) or zircono-silicates from Grace such as SP189043 (silica with 1.69% $ZrO_2$). More generally, suitable support materials may include up to about 50% $TiO_2$; more preferably between about 0.01% and about 25% $TiO_2$; and most preferably between about 0.1 and about 5% $TiO_2$. Also, suitable support materials may include up to about 50% $ZrO_2$; more preferably between about 0.01% and about 25% $ZrO_2$; and most preferably between about 0.1 and about 5% $ZrO_2$.

In another embodiment, it is contemplated to employ at least a plural combination of support materials, each with a different characteristic. For example, at least two support materials (e.g. zirconia and silica) with different characteristics may exhibit different activities and $CO_2$ selectivities, thus permitting preparation of catalysts with a desired set of characteristics, i.e. activity of a catalyst may be balanced against the $CO_2$ selectivity of the catalyst.

Layered Support Materials

In one embodiment, plural different supports are employed in a layered configuration as discussed in U.S. Patent Publication 2005/0181940, which is hereby incorporated by reference. Layering may be achieved in any of a number of different approaches, such as a plurality of lamella that are generally flat, undulated or a combination thereof. One particular approach is to utilize successively enveloping layers relative to an initial core layer. In general, herein, layered support materials typically include at least an inner layer and an outer layer at least partially surrounding the inner layer. All the layers of a layered catalyst may be modified as discussed below, with at least the outer layer preferably being modified.

The outer layer also preferably contains substantially more of catalytic components than the inner layer. In one embodiment, the inner and outer layers are made of different materials; but the materials may be the same. While the inner layer may be non-porous, other embodiments include an inner layer that is porous.

The layered support material preferably results in a form of a shell catalyst. But the layered support material offers a well defined boundary between the areas of the support material that have catalytic components and the areas that do not. Also, the outer layer can be constructed consistently with a desired thickness. Together the boundary and the uniform thickness of the outer layer result in a shell catalyst that is a shell of catalytic components that is of a uniform and known thickness.

Several techniques are known for creating layered support materials includes those described in U.S. Pat. Nos. 6,486,370; 5,935,889; and 5,200,382, each of which is incorporated by reference. In one embodiment, the materials of the inner layer are also not substantially penetrated by liquids, e.g., metals including but not limited to aluminum, titanium and zirconium. and zirconium. Examples of other materials for the inner layer include, but are not limited to, silica, alumina, silica-alumina, titania, titano-silicate, zirconia, zircono-silicate, niobia, silicates, alumino-silicates, titanates, spinel, silicon carbide, silicon nitride, carbon, cordierite, steatite, bentonite, clays, metals, glasses, quartz, pumice, zeolites, non-zeolitic molecular sieves combinations thereof and the like. A preferred inner layer is silica and KA160, in particular.

These materials which make up the inner layer may be in a variety of forms such as regularly shaped particulates, irregularly shaped particulates, pellets, discs, rings, stars, wagon wheels, honeycombs or other shaped bodies. A spherical particulate inner layer is preferred. The inner layer, whether spherical or not, has an effective diameter of about 0.02 mm to about 10.0 mm and preferably from about 0.04 mm to about 8.0 mm.

The outermost layer of any multilayer structure is one which is porous, has a surface area in the range of about 5 $m^2/g$ to about 300 $m^2/g$. The material of the outer layer is a metal, ceramic, or a combination thereof, and in one embodiment it is selected from alumina, silica, silica-alumina, titania, zirconia, niobia, silicates, aluminosilicates, titanates, spinel, silicon carbide, silicon nitride, carbon, cordierite, steatite, bentonite, clays, metals, glasses, quartz, pumice, zeolites, non-zeolitic molecular sieves and combinations thereof and preferably include alumina, silica, silica/alumina, zeolites, non-zeolite molecular sieves (NZMS), titania, zirconia and mixtures thereof. Specific examples include zirconia, silica and alumina or combinations thereof.

While the outer layer typically surrounds substantially the entire inner layer, this is not necessarily the case and a selective coating on the inner layer by the outer layer may be employed.

The outer layer may be coated on to the underlying layer in a suitable manner. In one embodiment, a slurry of the outer layer material is employed. Coating of the inner layer with the slurry may be accomplished by methods such as rolling, dipping, spraying, wash coating, other slurry coating techniques, combinations thereof or the like. One preferred technique involves using a fixed or fluidized bed of inner layer particles and spraying the slurry into the bed to coat the particles evenly. The slurry may be applied repeatedly in small amounts, with intervening drying, to provide an outer layer that is highly uniform in thickness.

The slurry utilized to coat the inner layer may also include any of a number of additives such as a surfactant, an organic or inorganic bonding agent that aids in the adhesion of the outer layer to an underlying layer, or combinations thereof. Examples of this organic bonding agent include but are not limited to PVA, hydroxypropylcellulose, methyl cellulose, and carboxymethylcellulose. The amount of organic bonding agent which is added to the slurry may vary, such as from about 1 wt % to about 15 wt % of the combination of outer layer and the bonding agent. Examples of inorganic bonding agents are selected from an alumina bonding agent (e.g. Bohmite), a silica bonding agent (e.g. Ludox, Teos), zirconia bonding agent (e.g. zirconia acetate or colloidal zirconia) or combinations thereof. Examples of silica bonding agents include silica sol and silica gel, while examples of alumina bonding agents include alumina sol, bentonite, Bohmite, and aluminum nitrate. The amount of inorganic bonding agent may range from about 2 wt % to about 15 wt % of the combination of the outer layer and the bonding agent. The thickness of the outer layer may range from about 5 microns to about 500 microns and preferably between about 20 microns and about 250 microns.

Once the inner layer is coated with the outer layer, the resultant layered support will be dried, such as by heating at a temperature of about 100° C. to about 320° C. (e.g. for a time of about 1 to about 24 hours) and then may optionally be calcined at a temperature of about 300° C. to about 900° C. (e.g. for a time of about 0.5 to about 10 hours) to enhance bonding the outer layer to it underlying layer over a least a portion of its surface and provide a layered catalyst support. The drying and calcining steps can be combined into one step. The resultant layered support material may be contacted with catalytic components just as any other support material in the production of catalysts, as described below. Alternately, the outer layer support material is contacted to catalytic components before it is coated onto the underlying layer.

In another embodiment of the layered support, a second outer layer is added to surround the initial outer layer to form at least three layers. The material for the second outer layer may be the same or different than the first outer layer. Suitable materials include those discussed discussed with respect to the first outer layer. The method for applying the second outer layer may be the same or different than the method used to apply the middle layer and suitable methods include those discussed with respect to the first outer layer. Organic or inorganic bonding agents as described may suitably used in the formation of the second outer layer.

The initial outer layer may or may not contain catalytic components. Similarly, the second outer layer may or may not contain catalytic components. If both outer layers contain catalytic component, then preferably different catalytic components are used in each layer, although this is not necessarily the case. In one preferred embodiment, the initial outer layer does not contain a catalytic component. Contacting catalytic component to the outer layers may be accomplished by impregnation or spray coating, as described below.

In embodiments where the initial outer layer contains catalytic component, one method of achieving this is to contact the catalytic component to the material of the initial outer layer before the material is applied to the inner layer. The second outer layer may be applied to the initial outer layer neat or containing catalytic component.

Other suitable techniques may be used to achieve a three layered support material in which one or more of the outer layers contain catalytic components. Indeed, the layered support material is not limited to three layers, but may include four, five or more layers, some or all of which may contain catalytic components.

In addition, the number and type of catalytic components that vary between the layers of the layered support material, other characteristics (e.g. porosity, particle size, surface area, pore volume, or the like) of the support material may vary between the layers.

Modified Support Materials

In another embodiment, the support material may be a modified support material. A modified support material is one that includes a modifier. The modifier is preferably a metal selected from alkali metals, alkaline earth metals, transition metals, and lanthanides. More preferably the modifier is selected from group 1 to 6 elements. Of these elements, barium, magnesium, cerium, potassium, calcium, niobium, tantalum, titanium, yttrium, strontium, zirconium, lanthanum, praseodymium, vanadium, molybdenum, and rubidium are more preferred. preferred. Niobium, titanium, magnesium, and zirconium represent the preferred modifiers, with zirconium being slightly less preferred. Combinations of these elements are also suitable with binary combinations the preferred type of combination. For example, suitable binary combinations include Ti—Zr, Mg—Nb, Nb—Zr, Mg—Ti, Nb—Ti, Mg—Zr or the like. Ratios of metals in the binary combinations range from about 4:1 to about 1:4.

Support materials are typically modified before catalytic components are added to the support material. In one preferred embodiment, a support material is impregnated with one or more aqueous solution of the modifiers (referred to as modifier precursor solutions). The physical state of the support material during the contacting step may be a dry solid, a slurry, a sol-gel, a colloidal suspension or the like.

In one embodiment, the modifiers contained in the precursor solution are water soluble salts made of the modifiers, including but not limited to, chlorides, other halides, nitrates, nitrites, hydroxides, oxides, oxalates, lactates, acetates (OAc), ammoniums and amines, with chloride free salts being preferred, with lactates, oxalates and nitrates being most preferred. Examples of modifier salts suitable for use in modifier precursor solutions include $Ba(NO_3)_2$, $Mg(NO_3)_2.6H_2O$, $Ce(NO_3)_3.6H_2O$, $KNO_3$, $Ca(NO_3)_2.4H_2O$, $(NH_4)_{1.35}Nb(C_2O_4)_{2.73}$, $Ta(C_2O_4)_{2.5}$, $Ti(CH_3CH(O\text{—})CO_2NH_4)_2(OH)_2$, $Y(NO_3)_3.6H_2O$, $ZrO(NO_3)_2.xH_2O$.

Furthermore, more than one salt may be used in a given modifier precursor solution. Precursor solutions typically may be made by dissolving the selected salt or salts in water, with or without solubility modifiers such as acids, bases or other solvents. Other non-aqueous solvents may also be suitable.

The modifier precursor solutions may be impregnated onto the support material in a single impregnation, although support materials maybe impregnated multiple times with modifiers having low atomic weight (e.g. Mg) or limited solubility in water (e.g. Nb or Ba). If multiple modifiers are utilized, the impregnation may be simultaneous (e.g. co-impregnation) or sequential and support material may be impregnated through the use of one or multiple precursor solutions. Suitably, the amount of modifier impregnated on to the support material is between about 0.01 wt % and about 5.0 wt % of the support material, and preferably between about 0.1 wt % and about wt % and about 4.0 wt %.

For the impregnating step, the volume of precursor solution may be selected so that it corresponds to up to about 110% of the pore volume of the support material. Volumes between about 95% and about 100% of the pore volume of the support material are preferred Typically, the modifier precursor solution is added to the support material and the support material is allowed absorb the precursor solution. This may be done drop wise until incipient wetness of the support material is substantially achieved. Alternatively, the support material may be placed by aliquots or batch wise into the precursor solution. A roto-immersion or other assistive apparatus may be used to achieve thorough contact between the support material and the precursor solution. Further, a spray device may be used such that the precursor solution is sprayed through a nozzle onto the support material, where it absorbed. A fixing step is typically not used to fix the modifier on to the support material, although this is not necessarily the case.

The modifier may be distributed all throughout the support material, distributed as a shell, and as an egg white or as an egg-yolk. Other contacting techniques may be used. For example, modifiers may be contacted to a support material through a chemical vapor deposition process, such as described in US2001/0048970, which is incorporated by reference. Also, spray coating or otherwise layering a uniformly pre-impregnated support material, as an outer layer, on to an inner layer may be suitable.

After the modifier precursor solution has been contacted to the support material, decanting, heat or reduced pressure may be used to remove any excess liquid not absorbed by the support material or to dry the support material.

After at least one modifier has been contacted to the support material, a calcining step may also be employed. The calcining step typically is before the catalytic components are contacted to the modified support material. The calcining step includes heating the support material in a non-reducing atmosphere (i.e. oxidizing or inert). During calcination, the modifiers on the support material are at least partially decomposed from their salts to a mixture of their oxide and free metal form.

For example, the calcining step is carried out at a temperature in the range of about 100° C. to about 900° C., preferably between about 300° C. and about 700° C. Non-reducing gases used for the calcination may included one or more inert or oxidizing gases such as helium, nitrogen, argon, neon, nitrogen oxides, oxygen, air, carbon dioxide, combinations thereof or the like. In one embodiment, the calcining step is carried out in an atmosphere of substantially pure nitrogen, oxygen, air or combinations thereof. Calcination times may vary but preferably are between about 1 and 5 hours. The degree of decomposition of the modifier salts depends on the temperature used and length of time the modified support material is calcined and can be followed by monitoring volatile decomposition products.

Methods of Making Catalysts

In general the method includes contacting modified support material with catalytic components and reducing the catalytic components. Preferred methods of the present invention include impregnating the catalytic components into the support material, calcining the catalytic component containing support material, reducing the catalytic components and activating the reduced catalytic components on the support material. Additional steps such as fixing the catalytic components on the support material and washing the fixed catalytic components may also be included in the method of making the catalyst or pre-catalyst. Some of the steps listed above are optional and others may be eliminated (e.g. the washing/fixing steps). In addition, some steps may be repeated (e.g. multiple impregnation or fix steps) and the order of the steps may be different from that listed above (e.g. the reducing step precedes the calcining step). To a certain extent, the contacting step will determine what later steps are needed for the formation of the catalyst.

Contacting Step

One particular approach to contacting is one pursuant to which an egg yolk catalyst or pre-catalyst is formed, an egg white catalyst or pre-catalyst is formed, an all throughout catalyst or pre-catalyst is formed or a shell catalyst or pre-catalyst is formed, or a combination thereof. In one embodiment, techniques that form shell catalysts are preferred.

The contacting step may be carried out using any of the modified support materials described above, with niobium, titanium and magnesium modifiers on support materials containing zirconia being the most favored. The contacting step is preferably carried out at ambient temperature and pressure conditions; however, reduced or elevated temperatures or pressures may be employed.

In one preferred contacting step, a modified support material is impregnated with one or more aqueous solutions of the catalytic components (referred to as catalytic precursor solutions). The physical state of the support material during the contacting step may be a dry solid, a slurry, a sol-gel, a colloidal suspension or the like.

In one embodiment, the catalytic components contained in the precursor solution are water soluble salts made of the catalytic components, including but not limited to, chlorides, other halides, nitrates, nitrites, hydroxides, oxides, oxalates, acetates (OAc), and amines, with halide free salts being preferred and chloride free salts being more preferred. Examples of palladium salts suitable for use in precursor solutions include $PdCl_2$, $Na_2PdCl_4$, $Pd(NH_3)_2(NO_2)_2$, $Pd(NH_3)_4(OH)_2$, $Pd(NH_3)_4(NO_3)_2$, $Pd(NO_3)_2$, $Pd(NH_3)_4(OAc)_2$, $Pd(NH_3)_2(OAc)_2$, $Pd(OAc)_2$ in KOH and/or $NMe_4OH$ and/or NaOH, $Pd(NH_3)_4(HCO_3)_2$ and palladium oxalate. Of the chloride-containing palladium precursors, $Na_2PdCl_4$ is most preferred. Of the chloride free palladium precursor salts, the following four are the most preferred: $Pd(NH_3)_4(NO_3)_2$, $Pd(NO_3)_2$, $Pd(NH_3)_2(NO_2)_2$, $Pd(NH_3)_4(OH)_2$. Examples of gold salts suitable for use in precursor solution include $AuCl_3$, $HAuCl_4$, $NaAuCl_4$, $KAuO_2$, $NaAuO_2$, $NMe_4AuO_2$, $Au(OAc)_3$ in KOH and/or $NMe_4OH$ as well as $HAu(NO_3)_4$ in nitric acid, with $KAuO_2$ being the most preferred of the chloride free gold precursors.

Furthermore, more than one salt may be used in a given precursor solution. For example, a palladium salt may be combined with a gold salt or two different palladium salts may be combined together in a single precursor solution. Precursor solutions typically may be made by dissolving the selected salt or salts in water, with or without solubility modifiers such as acids, bases or other solvents. Other non-aqueous solvents may also be suitable.

The precursor solutions may be impregnated onto the support material simultaneously (e.g. co-impregnation) or sequentially and may be impregnated through the use of one or multiple precursor solutions. In addition, a catalytic component may be impregnated on to support material in multiple steps, such that a portion of the catalytic component is contacted each time. For example, one suitable protocol may include impregnating with Pd, followed by impregnating with Au, followed by impregnating again with Au. In another protocol, Pd and Au are preferably co-impregnated.

The order of impregnating the modified support material with the catalytic precursor solutions is not critical; although there may be some advantages to certain orders, as discussed below, with respect to the calcining step. Preferably, the palladium catalytic component is impregnated onto the support material first, with gold being impregnated after palladium, or last. Also, the support material may be impregnated multiple times with the same catalytic component. For example, a portion of the overall gold contained in the catalyst may be first contacted, followed by contacting of a second portion of the gold. One more other steps may intervene between the steps in which gold is contacted to the support material, e.g. calcining, reducing, and/or fixing.

The acid-base profile of the precursor solutions may influence whether a co-impregnation or a sequential impregnation is utilized. Thus, only precursor solutions with similar acid-base profile should be used together in a co-impregnating step; this eliminates any acid-base reactions that may foul the precursor solutions For the impregnating step, the volume of precursor solution is selected so that it corresponds to between about 85% and about 110% of the pore volume of the support material. Volumes between about 95% and about 100% of the pore volume of the support material are preferred. Further, for one step fixing and modifying discussed below, the modifier precursor solution may make up a lower percentage of pore volume. For example, less than 50% of the pore volume, less than 25% of the pore volume or less than 10% of the pore volume.

Typically, the precursor solution is added to the support material and the support material is allowed absorb the precursor solution. This may be done drop wise until incipient wetness of the support material is substantially achieved. Alternatively, the support material may be placed by aliquots or batch wise into the precursor solution. A roto-immersion or other assistive apparatus may be used to achieve thorough contact between the support material and the precursor solution. Further, a spray device may be used such that the precursor solution is sprayed through a nozzle onto the support material, where it absorbed. Optionally, decanting, heat or reduced pressure may be used to remove any excess liquid not absorbed by the support material or to dry the support material after impregnation.

Other contacting techniques may be used to avoid a fixing step while still achieving a shell catalyst. For example, catalytic components may be contacted to a support material through a chemical vapor deposition process, such as described in US2001/0048970, which is incorporated by reference. Also, spray coating or otherwise layering a uniformly pre-impregnated support material, as an outer layer, on to an inner layer effectively forms shell catalyst that may also be described as a layered support material. In another technique, organometallic precursors of catalytic components, particularly with respect to gold, may be used to form shell catalysts, as described in U.S. Pat. No. 5,700,753, which is incorporated by reference.

A physical shell formation technique may also be suitable for the production of shell catalysts. Here, the precursor solution may be sprayed onto a heated modified support material or a layered modified support material, where the solvent of the precursor solution evaporates upon contact with the heated support material, thus depositing the catalytic components in a shell on the support material. Preferably, temperatures between about 40 and 140° C. may be used. Selecting the temperature of the support material and the flow rate of the solution through the spray nozzle may be used control the thickness of the shell. For example, with temperatures above about 100° C., a relatively thin shell is formed. This embodiment may be particularly useful when chloride free precursors are utilized to help enhance the shell formation on the support material. See for example U.S. Patent Publication 20050181940.

One skilled in the art will understand that a combination of the contacting steps may be an appropriate method of forming a contacted support material.

Fixing Step

It may be desirable to transform at least a portion of the catalytic components on the contacted and modified support material from a water-soluble form to a water-insoluble form. Such a step may be referred to as a fixing step. This may be accomplished by applying a fixing agent (e.g. dispersion in a liquid, such as a solution) to the impregnated support material which causes at least a portion of the catalytic components to precipitate. This fixing step helps to form a shell catalyst, but is not required to form shell catalysts.

Any suitable fixing agent may be used, with hydroxides (e.g. alkali metal hydroxides), silicates, borates, carbonates and bicarbonates in aqueous solutions being preferred. The preferred fixing agent is NaOH. Fixing may be accomplished by adding the fixing agent to the support material before, during or after the precursor solutions are impregnated on the support material. Typically, the fixing agent is used subsequent to the contacting step such that the contacted support material is allowed to soak in the fixing agent solution for about 1 to about 24 hours. The specific time depends upon the combination of the precursor solution and the fixing agent. Like the impregnating step, an assistive device, such as a roto immersion apparatus as described in U.S. Pat. No. 5,332,710, which is incorporated herein by reference, may advantageously be used in the fixing step.

The fixing step may be accomplished in one or multiple steps, referred as a co-fix or a separate fix. In a co-fix, one or more volumes of a fixing agent solution is applied to the contacted support material after all the relevant precursor solutions have been contacted to the support material, whether the contact was accomplished through the use of one or multiple precursor solutions. For example, fixing after sequential impregnation with a palladium precursor solution and a gold precursor solution would be a co-fix. An example of co-fixing may be found in U.S. Pat. No. 5,314,888, which is incorporated by reference.

A separate fix, on the other hand, would include applying a fixing agent solution during or after each impregnation with a precursor solution. For example, the following protocols would be a separate fix: a) impregnating palladium followed by fixing followed by impregnating with gold followed by fixing; or b) co-impregnating with palladium followed by fixing followed fixing followed by impregnating with gold followed by fixing. Between a fix and subsequent impregnation, any excess liquid may be removed and the support material dried, although this is not necessarily the case. An example of separate fixing may be found in U.S. Pat. No. 6,034,030, which is incorporated by reference.

In another embodiment, the fixing step and the contacting step are conducted simultaneously, one example of which is described in U.S. Pat. No. 4,048,096, which is incorporated by reference. For example, a simultaneous fix might be: impregnating with palladium followed by fixing followed by impregnating with gold and fixing agent. In a variation on this embodiment, the fix may be conducted twice for a catalytic component. A catalytic component may be partially fixed when it is contacted to the support material (called a "prefix"), followed an additional, final fix. For example: impregnating with palladium followed by impregnating with gold and a pre-fixing agent followed by fixing with a final fixing agent. This technique may be used to help insure the formation of shell type catalyst as opposed to an all throughout catalyst.

In another embodiment of the simultaneous fixing and contacting step, the fixing solution is impregnated into the modified support material such that between about 25 and about 95% of the pore volume is filled. Preferably, between about 70 and about 90% of the pore volume is filled by the fixing solution. The remainder of the pore volume is then filled with the catalytic precursor solution. Step-wise or co-impregnation of the catalytic precursor may be used. This simultaneous fix and contacting step avoids the need for a drying step, thus simplifying the process. Examples of fixing solutions include those comprising alkali metal hydroxides, alkali metal carbonates, alkali metal bicarbonates or mixtures thereof. The fixing solutions may also be buffered to help maintain the pH of the solution.

In another embodiment, particularly suitable for use with chloride free precursors, the modified support material is pre-treated with a fixing agent to adjust the properties of the support material. In this embodiment, the support material is first impregnated with either an acid or base solution, typically free of metals. After drying, the support material is impregnated with a precursor solution that has the opposite acidity/alkalinity as the dried support material. The ensuing acid-base reaction forms a shell of catalytic components on the support material. For example, nitric acid may be used to pre-treat a support material that in turn is impregnated with a basic precursor solution such as $Pd(OH)_2$ or $Au(OH)_3$. This formation technique may be considered as using a fixing step followed by a contacting step.

In another embodiment, the modified support may be pre-treated before impregnation of the Pd and or Au in order to neutralize potentially chemically reactive sites on the support material which may cause poor shell formation. For example, a basic support (e.g. zirconia) may be pre-treated with HCl to neutralize selected sites, followed by with Pd and Au impregnation and by fixing with base.

The concentration of fixing agent in the solution is typically a molar excess of the amount of catalytic components impregnated on the support material. The amount of fixing agent should be between about 1.0 to about 3.0, preferably about 1.1 to about 2.0 times the amount necessary to react with the catalytically active cations present in the water-soluble salt.

The volume of fixing agent solution supplied generally should be an amount sufficient to cover the available free surfaces of the impregnated support material This may be accomplished by introducing, for example, a volume that is greater than the pore volume of the contacted support material.

The combination of impregnating and fixing steps can form a shell type catalyst. But, the use of halide free precursor solutions also permits the formation of a shell catalyst while optionally eliminating the fixing step. In the absence of a chloride precursor, a washing step, as discussed below, may be obviated. Further, the process can be free of a step of fixing catalytic components that would otherwise be needed to survive the washing step. Because no washing step is needed, the catalytic components need not be fixed to survive the washing step. Subsequent steps in the method making the catalyst do not require the catalytic components be fixed and thus the remainder of the step maybe carried out without additional preparatory steps. Overall, the use of chloride free precursors permits a catalyst or pre-catalyst production method that is free of a step of washing, thus reducing the number of steps needed to produce the catalyst and eliminating the need to dispose of chloride containing waste.

Washing Step

Particularly, when halide containing precursor solutions are utilized and in other applications as desired, after the fixing step, the fixed support material may be washed to remove any halide residue on the support or otherwise treated to eliminate the potential negative effect of a contaminant on the support material. The washing step included rinsing the fixed support material in water, preferably deionized water. Washing may be done in a batch or a continuous mode. Washing at room temperature should continue until the effluent wash water has a halide ion content of less than about 1000 ppm, and more preferably until the final effluent gives a negative result to a silver nitrate test. The washing step may be carried out after or simultaneously with the reducing step, discussed below, but preferably is carried out before. As discussed above, the use of halide free precursor solutions permits the elimination of the washing step.

Calcining Step of Catalytic Components

After at least one catalytic component has been contacted to the support material, one or more a calcining steps may be employed, although this is not necessarily the case and in some instances is not preferred. The calcining step typically is before the reducing step and after the fixing step (if such a step is used) but may take place elsewhere in the process. In another embodiment, the calcining step is carried out after the reducing step. The calcining step includes heating the support material in a non-reducing atmosphere (i.e. oxidizing or inert). During calcination, the catalytic components on the modified support material are at least partially decomposed from their salts to a mixture of their oxide and free metal form.

For example, the calcining step is carried out at a temperature in the range of about 100° C. to about 700° C., preferably between about 200° C. and about 500° C. Non-reducing gases used for the calcination may included one or more inert or oxidizing gases such as helium, nitrogen, argon, neon, nitrogen oxides, oxygen, air, carbon dioxide, combinations thereof or the like. In one embodiment, the calcining step is carried out in an atmosphere of substantially pure nitrogen, oxygen, air or combinations thereof. Calcination times may vary but preferably are between about 1 and 5 hours. The degree of decomposition of the catalytic component salts depends on the temperature used and length of time the impregnated catalyst is calcined and can be followed by monitoring volatile decomposition products. Optionally, on zirconia support materials, only the Pd is calcined.

Reducing Step

Another step employed generally herein to at least partially transform any remaining catalytic components from a salt or oxide form to a catalytically active state, such as by a reducing step. Typically this is done by exposure of salts or oxides to a reducing agent, examples of which include ammonia, carbon monoxide, hydrogen, hydrocarbons, olefins, aldehydes, alcohols, hydrazine, primary amines, carboxylic acids, carboxylic acid salts, carboxylic acid esters and combinations thereof. Hydrogen, ethylene, propylene, alkaline hydrazine and alkaline formaldehyde and combinations thereof are preferred reducing agents with ethylene and hydrogen blended with inert gases particularly preferred. Although reduction employing a gaseous environment is preferred, a reducing step carried with a liquid environment may also be used (e.g. employing a reducing solution). The temperature selected for the reduction can range from ambient up to about 550° C. Reduction times will typically vary from about 1 to about 10 hours, with 5 hours preferred.

Since the process used to reduce the catalytic components may influences the characteristics of the final catalyst, conditions employed for the reduction may be varied depending on whether high activity, high selectivity or some balance of these properties is desired.

In one embodiment, palladium is contacted to the support material, fixed and reduced before gold is contacted and reduced, as described in U.S. Pat. Nos. 6,486,093, 6,015,769 and related patents, all of which are incorporated by reference.

Exemplary protocols including a reducing step include: a) impregnating with palladium followed by optionally calcining followed by impregnating with gold followed by reducing; b) co-impregnating with palladium and gold followed by optionally calcining followed by reducing; or c) impregnating with palladium followed by optionally calcining followed by reducing followed by impregnating with gold.

Activating Step

Usually after the reducing step and before the catalyst is used, an activating step is desirable. While the catalyst may be used without the activating step, the step has several beneficial results, including lengthening the operational life time of the catalyst. The activating step may be accomplished in accordance with conventional practice. Namely, the reduced support material is contacted with an activating agent, such as an alkali metal salt (e.g. carboxylate and/or alkali metal hydroxide), prior to use. Conventional alkali metal carboxylates such as the sodium, potassium, lithium and cesium salts of $C_{2-4}$ aliphatic carboxylic acids are employed for this purpose. A preferred activating agent in the production of VA is an alkali acetate, with potassium acetate (KOAc) being the most preferred.

The support material may optionally be impregnated with a solution of the activating agent. After drying, the catalyst may contain, for example, about 10 to about 70 grams, preferably about 20 to about 60 grams of activating agent per liter of catalyst.

Methods of Making Alkenyl Alkanoates

The present invention may be utilized to produce alkenyl alkanoates from an alkene, alkanoic acid and an oxygen containing gas in the presence of a catalyst. Preferred alkene starting materials contain from two to four carbon atoms (e.g. ethylene, propylene and n-butene). Preferred alkanoic acid starting materials used in the process of this invention for producing alkenyl alkanoates contain from two to four carbon atoms (e.g., acetic, propionic and butyric acid). Preferred products of the process are VA, vinyl propionate, vinyl butyrate, and allyl acetate. The most preferred starting materials are ethylene and acetic acid with the VA being the most preferred product. Thus, the present invention is useful in the production of olefinically unsaturated carboxylic esters from an olefinically unsaturated compound, a carboxylic acid and oxygen in the presence of a catalyst. Although the rest of the specification discusses VA exclusively, it should be understood that the catalysts, method of making the catalysts and production methods are equally applicable to other alkenyl alkanoates, and the description is not intended as limiting the application of the invention to VA.

When VA is produced using the catalyst of the present invention, a stream of gas, which contains ethylene, oxygen or air, and acetic acid is passed over the catalyst. The composition of the gas stream can be varied within wide limits, taking in account the zone of flammability of the effluent. For example, the molar ratio of ethylene to oxygen can be about 80:20 to about 98:2, the molar ratio of acetic acid to ethylene can be about 100:1 to about 1:100, preferably about 10:1 to 1:10, and most preferably about 1:1 to about 1:8. The gas stream may also contain gaseous alkali metal acetate and/or inert gases, such as nitrogen, carbon dioxide and/or saturated hydrocarbons. Reaction temperatures which can be used are elevated temperatures, preferably those in the range of about 125-220° C. The pressure employed can be a somewhat reduced pressure, normal pressure or elevated pressure, preferably a pressure of up to about 20 atmospheres gauge.

In addition to fixed bed reactors, the methods of producing alkenyl alkanoates and the catalyst of the present invention may also be suitably employed in other types of reaction, for example, fluidized bed reactors.

The methods of VA production preferably achieve an EA/VA ratio of less than about 800 ppm, more preferably less than about 400 ppm, more preferably less than about 250 ppm and most preferably less than about 200 ppm. The methods also preferably achieve a $CO_2$ selectivity of less than about 10%, and more preferably less than about 9% and most preferably less than 8% when the $O_2$ conversion is 45%. Most preferably, the catalyst will have both the EA/VA ratio and $CO_2$ selectivity discussed above.

Moreover, the present methods of VA production preferably result in maintained or improved $CO_2$ selectivities as compared to a standard catalyst utilized in similar processing conditions. A standard catalyst is any catalyst that may be used as a control, and preferably does not include a modified support material. To make the comparison, the standard catalyst is used as a control in the same or similar processing conditions as processing conditions for the modified support material catalyst. The catalyst on the modified support material need only match (or improve upon) the $CO_2$ selectivity of the standard catalyst at a given $O_2$ conversion. One example of a catalyst that may be used as a standard catalyst is shown in U.S. Pat. No. 5,332,710, hereby U.S. Pat. No. 5,332,710, hereby incorporated by reference.

Examples of Catalysts on Modified Support Materials

Combinatorial/High Throughput chemistry and analysis techniques were utilized to screen catalysts with modified support materials. The compositional space for the screened catalysts included those with gold and palladium as catalytic components where the atomic ratio of gold to palladium is between 0.3 to 1.2. Support materials included: KA-160 (silica-alumina), Norpro XZ 16052 (zirconia), Aerolyst 350 (silica), Grace SP-9600 (silica), Grace SP-9601 (silica), Grace SP-9599 (silica), Grace SP-9602 (silica), Grace SP 189043.USA3 (zircono-silica), Grace SP18-9534 (titano-silicate), Norpro XZ 16075 (zirconia) and Norpro XZ 16052 (zirconia). The above support materials were modified with Ba, Mg, Ce, K, Ca, Nb, Ta, Ti, Y, Sr, Z, La, Pr, V, Mo, Rb, and selected bimetallic combinations discussed above. Unmodified support materials were also tested as controls.

Modified support materials other than zirconia were prepared by impregnating 0.5 g samples of support (dried at 120° C. for at least 2 h) to incipient wetness with modifier precursor solutions to achieve one of three levels: 1.0, 2.0 and 4.0 wt %. This was followed by drying at 105° C. for at least 2 h and calcination at 500° C., with 2° C./min heating rate. A robot from Hamilton was used to do all liquid dispensing The modified support materials were impregnated to incipient wetness with a solution of $Pd(NH_3)_4(OH)_2$ to a Pd loading of 42.6 g Pd/L catalyst. During and after impregnation, the support materials were homogenized for at least 1 h. After impregnation, the support materials were dried in air at 105° C. for at least 2 h, and then calcined in air at 350° C. for 2 h, with a heating rate of 2° C./min.

Next, the modified support materials were impregnated to incipient wetness with freshly prepared 1 M [KOH+Au(OH)$_3$] solution to achieve Au:Pd ratios of 0.45, 0.6, 0.9, and 1.2. During and after impregnation, the impregnated support materials were homogenized for at least 1 h, followed by drying in air at 105° C. for at least 2 h.

The modified support materials with the catalytic components were reduced in 7% hydrogen in nitrogen. The samples were placed in small crucibles in which the catalyst bed was about 1 to 3 mm deep. A flow of 100 mL was maintained throughout the reduction, with a 2° C./min heating rate, 5 h at 350° C. After reduction, the samples were activated by impregnation with a KOAc solution to 40 g KOAc/L catalyst and dried at 105° C. for at least 2 h.

Modified zirconia support materials were made using essentially that same procedure as discussed above, except that no calcination took place after Pd impregnation and the reduction utilized 5% ethylene in nitrogen at 150° C.

Catalysts prepared according to this protocol were heterogeneously diluted with support material containing 40 g/l KOAc to give an overall Pd loading of 7 g/l. The simulated shell catalysts were tested using a standard line-in protocol to test the catalysts' $CO_2$ selectivity and EA/VA ratios using a parallel reactor system. The standard protocol included testing the catalysts for 8 hours under normal feeds at 145° C. (13.8% HOAc, 40% $C_2H_4$, 7.9% $O_2$ and 38% $N_2$, P=10 atm, SV=138 cc/min/cc catalyst). A temperature ramp of 155° C., 165° C., 175° C. and 145° C. was then used to obtain information on each catalyst. Catalysts that showed $CO_2$ selectivity less than about 9.0% at 45% $O_2$ conversion and an EA/VA ratio of less than 800 ppm were deemed acceptable.

Catalysts on modified support materials that showed acceptable $CO_2$ selectivity and EA/VA ratios are shown in the table below:

| Support material | Name | Ta | Nb | Ti | Y | Zr | Mg | Pr | La |
|---|---|---|---|---|---|---|---|---|---|
| silica-alumina | KA-160 | x | x | x | x | x | x | | |
| zircono-silicate | Grace SP 189043.USA3 | | x | x | | x | | | |
| silica | Aerolyst 350 | | | | x | | x | | |
| titano-silicate | Grace SP 18-9534 | x | x | | | x | x | | |
| silica | Grace SP-9601 | | | | | x | | x | x |
| zirconia | Norpro XZ 16075 | x | x | x | x | x | | | x |
| zirconia | Norpro XZ 16052 | x | x | | | x | | | |

Based on the results above, other levels of modifier (e.g. 0.1 wt % and 0.4 wt %) and/or other Au:Pd ratios were tested to optimize the $CO_2$ selectivity and the EA/VA ratio. Furthermore, variations in catalyst preparation conditions were also tested (e.g. different calcination temperatures, impregnation methods and/or different reduction conditions).

To differentiate between the acceptable catalysts, a high temperature deactivation test was used. Normal feeds (13.8% HOAc, 40% $C_2H_4$, 7.9% $O_2$ and 38% $N_2$, P=10 atm, SV=138 cc/min/cc catalyst) were used for 8 hours at 180° C. as a line-in protocol. The line-in was followed by a temperature ramp of 165° C., 175° C., 185° C., 195° C. and 165° C. Catalysts that showed acceptable properties under a more stringent set of guidelines (e.g. an EA/VA ratio of less than about 250 ppm with acceptable $CO_2$ selectivity at 45% $O_2$ conversion) would be the most preferred of the catalysts on the modified support materials. Under this protocol, the most preferred modified supports include niobium, titanium and magnesium on zirconia support materials. Also preferred were titanium and zirconium modifiers on the titano-silicate.

Comparison of catalysts with and without modified support materials may be carried out using any VA synthetic procedure so long as the same procedure is used to test both types of catalysts. It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

We claim:

1. A method of producing vinyl acetate, comprising:
   contacting a feed comprising ethylene, acetic acid and an oxygen containing gas to a catalyst or pre-catalyst formed on a modified and calcined support material that results in vinyl acetate and at least one byproduct,
   wherein the support material is modified with 1) niobium, magnesium, tantalum, yttrium, lanthanum, or praseodymium and combinations thereof; or 2) titanium or zirconium and combinations thereof when the support material is selected from titano-silicate, zircono-silicate or zirconia.

2. The method of claim 1 wherein the byproduct includes ethyl acetate and the ratio of ethyl acetate to resultant vinyl acetate is less than about 800 ppm.

3. The method of claim 2 wherein the byproduct includes ethyl acetate and the ratio of ethyl acetate to resultant vinyl acetate is less than about 250 ppm.

4. The method of claim 1 wherein the catalyst or pre-catalyst has a $CO_2$ selectivity of less than about 9.0%.

5. The method of claim 4 wherein the catalyst or pre-catalyst has a $CO_2$ selectivity of less than about 9.0% at 45% $O_2$ conversion.

6. The method of claim 4 wherein the byproduct includes ethyl acetate and the ratio of ethyl acetate to resultant vinyl acetate is less than about 800 ppm and wherein the catalyst or pre-catalyst has a $CO_2$ selectivity of less than about 9.0%.

7. The method of claim 6 wherein the byproduct includes ethyl acetate and the ratio of ethyl acetate to resultant vinyl acetate is less than about 800 ppm and wherein the catalyst or pre-catalyst has a $CO_2$ selectivity of less than about 9.0% at 45% $O_2$ conversion.

8. The method of claim 4 wherein the byproduct includes ethyl acetate and the ratio of ethyl acetate to resultant vinyl acetate is less than about 250 ppm and wherein the catalyst or pre-catalyst has a $CO_2$ selectivity of less than about 9.0%.

9. The method of claim 8 wherein the byproduct includes ethyl acetate and the ratio of ethyl acetate to resultant vinyl acetate is less than about 250 ppm and wherein the catalyst or pre-catalyst has a $CO_2$ selectivity of less than about 9.0% at 45% $O_2$ conversion.

10. The method of claim 1 wherein the support material is modified with niobium, or magnesium or combinations thereof.

11. The method of claim 1 wherein the support material comprises zirconia.

12. The method of claim 1 wherein the support material comprises titano-silicate or zircono silicate.

13. The method of claim 1 wherein the support material is a layered support material.

14. The method of claim 1 wherein the support material is modified with titanium or zirconium or combinations thereof.

* * * * *